(12) United States Patent
Sonomoto et al.

(10) Patent No.: US 8,420,359 B2
(45) Date of Patent: Apr. 16, 2013

(54) METHOD OF PRODUCING BUTANOL

(75) Inventors: Kenji Sonomoto, Fukuoka (JP);
Mugihito Oshiro, Fukuoka (JP);
Katsuhiro Hanada, Fukuoka (JP)

(73) Assignees: Sumitomo Corporation, Tokyo (JP);
Kyushu University, National University Corporation, Fukuoka-Shi (JP)

( * ) Notice: Subject to any disclaimer, the term of this patent is extended or adjusted under 35 U.S.C. 154(b) by 0 days.

(21) Appl. No.: 13/128,190

(22) PCT Filed: Feb. 15, 2010

(86) PCT No.: PCT/JP2010/052226
§ 371 (c)(1),
(2), (4) Date: May 6, 2011

(87) PCT Pub. No.: WO2011/099165
PCT Pub. Date: Aug. 18, 2011

(65) Prior Publication Data
US 2011/0296747 A1    Dec. 8, 2011

(51) Int. Cl.
*C12P 7/16*    (2006.01)

(52) U.S. Cl.
USPC ............................................. 435/160

(58) Field of Classification Search ............ 435/160
See application file for complete search history.

(56) References Cited

U.S. PATENT DOCUMENTS 6,358,717 B1 *    3/2002    Blaschek et al. ............. 435/160

FOREIGN PATENT DOCUMENTS

KR    9102858    *    5/1991

OTHER PUBLICATIONS

Jones, et al., "Acetone-Butanol Fermentation Revisited ", Microbiological Reviews, pp. 484-524, Dec. 1986.
Shinto et al., "Kinetic Study of Substrate Dependency for Higher Butanol Production in Acetone-Butanol-Ethanol Fermentation", Process Biochemistry, vol. 43, Issue 12, pp. 1452-1461, Dec. 2008.
Tashiro et al., "High Butanol Production by *Clostridium saccharoperbutylacetonicum* N1-4 in Fed-Batch Culture with pH-Stat Continuous Butyric Acid and Glucose Feeding Method", Journal of Bioscience and Bioengineering, vol. 98, No. 4, pp. 263-268, 2004.
Tashiro et al., "Novel High-Efficient Butanol Production from Butyrate by Non-Growing *Clostridium saccharoperbutylacetonicum* N1-4 (ATCC 13564) with Methyl Viologen" Journal of Bioscience and Bioengineering, vol. 104, No. 3, pp. 238-240, 2007.
Tashiro et al., Kinetic Study of Acetone-Butanol-Ethanol Fermentation, A Doctor Thesis at Kyushu University, pp. 45-46, 63-65, 94-96, 119-121 and 123, 2006.
Tashiro et al., Seibutsu-Kogaku, vol. 87, No. 10, Society for Biotechnology, Japan, pp. 484-486, 2009.
Full English language translation of KR 9102858.
Gu et al., "Economical challenges to microbial producers of butanol: Feedstock, butanol ratio and titer," Biotechnol. J. 2011, 6, 1348-1357.
International Search Report dated Apr. 6, 2010 corresponding to PCT/JP2010/052226.
Liu et al. "Butanol production by *Clostridium beijerinckii* ATCC 55025 from wheat bran," J Ind Microbiol Biotechnol (2010) 37:495-501.
Oshiro et al., "The Collection of Abstracts of Lectures delivered in the 61st Annual Meeting of the Society for Biotechnology", Japan, Society for Biotechnology, 1Lp19, 2009.

* cited by examiner

*Primary Examiner* — Tekchand Saidha
(74) *Attorney, Agent, or Firm* — Birch, Stewart, Kolasch & Birch, LLP

(57) ABSTRACT

The present invention provides a method of producing butanol, comprising: causing a microorganism which belongs to the genus *Clostridium* and is capable of producing butanol to produce butanol in a medium comprising saccharides assimilable by a microorganism which belongs to the genus *Clostridium*, lactic acid and/or acetic acid as substrates. By the method of the present invention, the concentration of butanol produced in a culture medium (solution) can be increased and, furthermore, the rate of butanol production can also be increased. In the present invention, a mixture of D-lactic acid and L-lactic acid obtained by lactic acid fermentation or a fermentation product of hetero-lactic acid fermentation containing acetic acid as a by-product can be utilized. By combining lactic acid fermentation and the method of the present invention, a practical system of butanol production from inedible biomass which requires neither expensive enzyme nor advanced technology such as genetic manipulation can be constructed.

8 Claims, 3 Drawing Sheets

METHOD OF PRODUCING BUTANOL

TECHNICAL FIELD

The present invention relates to production of biobutanol by a microorganism of the genus *Clostridium*. In particular, the present invention relates to a method for the effective utilization of lactic and/or acetic acid in the production of biobutanol. In the present invention, lactic acid having low optical purity, hetero-lactic acid fermentation products containing acetic acid as a by-product, and inedible biomass can also be utilized effectively.

BACKGROUND ART

Biobutanol produced by a microorganism of the genus *Clostridium* has attracted great attention as post-bioethanol. As biobutanol production by a microorganism of the genus *Clostridium* also produces acetone and some ethanol simultaneously, it is also called acetone-butanol-ethanol fermentation (ABE fermentation). Compared with ethanol, butanol is advantageous in terms of energy density and physical properties such as low corrosiveness and hygroscopicity. Further, butanol not only can be used as a raw material of a chemically-synthesized substance such as isoprene, isobutene and butane, but also can be added to diesel fuel as well as gasoline fuel; butanol has a wide variety of uses.

On the other hand, ABE fermentation has a complex and unique metabolic pathway in which a metabolite is changed significantly depending on the state of bacteria (Non-patent Document 1). Further, since butanol inhibits growth of a production microorganism, fermentation productivity of butanol is significantly lower than that of ethanol, and there exist many technical problems which must be solved in order to improve productivity. Regarding biobutanol production, the present inventors have reported a system of production by pH-stat fed-batch culture with growing cells using butyric acid as a substrate (Non-patent Document 2), a highly-efficient system of production with resting cells (Non-patent Document 3) and the like.

On the other hand, the use of edible biomass such as corn or sugarcane as a raw material to produce biofuel or biomaterial by a microorganism has a problem that it will create a competition between biofuel and food-production, which leads to an increase in price. As a solution for this problem, production of a substance using inedible biomass as a raw material has drawn attention. While edible biomass contains a large amount of amylose and thus can easily be fermented, inedible biomass in general contains large amounts of cellulose and hemicellulose. Hence, the following approaches have been taken in the research on the use of inedible biomass: decomposition of cellulose or hemicellulose by saccharogenic amylose or the like into glucose or xylose, which can be used as a substrate fermentable by a microorganism; and acquisition of a microorganism that can use cellulose or hemicellulose directly as a substrate.

However, direct use of inedible biomass as a raw material in fermentation to produce biobutanol has not been accomplished.

CITATION LIST

Patent Documents

Non-patent Document 1: Jones, D. T. and Woods, D. R.: Microbiol. Rev., 50, 484-524 (1986)
Non-patent Document 2: Tashiro, Y. et al.: J. Biosci. Bioeng., 98, 263-268 (2004)
Non-patent Document 3: Tashiro, Y. et al.: J. Biosci. Bioeng., 104, 238-240 (2007)

SUMMARY OF INVENTION

Technical Problem

The present inventors have studied techniques for utilizing a microorganism to preserve food, pharmaceutical, and medium. They have studied not only ABE fermentation but also production of lactic acid for use as a polylactic acid material, which is a biodegradable, recyclable plastic, by fermentation using various characteristic lactic acid bacteria. Lactic acid with high optical activity produced by homofermentation is suitable for use as a polylactic acid material; in a case in which lactic acid is obtained as a mixture of D-lactic acid and L-lactic acid, or in a case in which lactic acid is produced by heterofermentation and contains acetic acid as a by-product, there may be another use. Further, techniques for utilizing inedible biomass in lactic acid fermentation have been developed, and if lactic acid fermentation can be combined with ABE fermentation, it will become possible to construct a practical system of butanol production from inedible biomass which requires neither an expensive enzyme nor advanced technology such as genetic manipulation.

Solution to Problem

In the metabolic pathway of a butanol-producing microorganism, an organic acid (acetic acid, butyric acid) is produced during a logarithmic growth phase, and the organic acid undergoes re-assimilation to produce a solvent (acetone-butanol-ethanol) during a stationary phase. From this fact, the present inventors considered that efficient butanol production using lactic acid or acetic acid might be accomplished by using the organic acid re-assimilation pathway of a microorganism in butanol production. As a result of intensive and extensive studies, they completed the present invention.

The present invention provides:

1) A method of producing butanol, comprising the step of allowing a microorganism which belongs to the genus *Clostridium* and is capable of producing butanol to produce butanol in a medium containing a saccharide assimilable by the microorganism of the genus *Clostridium*, lactic acid and/or acetic acid as substrates;

2) The method of 1), wherein the microorganism which belongs to the genus *Clostridium* is in a growing state, and the medium contains as substrates glucose and lactic acid;

3) The method of 1), wherein the microorganism which belongs to the genus *Clostridium* is in a resting state, and the medium contains as substrates glucose, lactic acid and acetic acid;

4) The method of any one of 1) to 3), wherein the microorganism which belongs to the genus *Clostridium* is *Clostridium saccharoperbutylacetonicum;*

5) The method of any one of 1) to 4), wherein the lactic acid is a mixture of L-lactic acid and D-lactic acid;

6) A method of producing butanol, comprising the steps of: allowing a lactic acid bacterium which is capable of homo-lactic acid fermentation and is capable of producing L-lactic acid and D-lactic acid, or a lactic acid bacterium which is capable of hetero-lactic acid fermentation to produce lactic acid and/or acetic acid from biomass material; and allowing a microorganism which belongs to the genus *Clostridium* and is capable of producing butanol to produce butanol in a medium containing, as substrates, a saccharide assimilable by the microorganism of the genus *Clostridium*, and the lactic acid and/or acetic acid thus produced;

7) The method of 6), wherein the biomass material is inedible biomass; and

8) A method of producing a butanol-containing fuel, comprising the steps for the method of producing butanol as defined in any one of 1) to 7), and adding the resulting butanol to a diesel fuel.

The present invention is a first report of butanol production using lactic acid and/or acetic acid as an auxiliary raw material. The present invention can improve the maximum concentration of produced butanol in the butanol production, and can increase the butanol production rate (the butanol production rate may be indicated in terms of g/l/h as a difference in concentration of butanol in a culture medium per unit time).

The present invention is also applicable to utilization of lactic acid having low optical purity, a hetero-lactic acid fermentation product containing acetic acid as a by-product, and inedible biomass.

DESCRIPTION OF EMBODIMENTS

[Butanol Production Using Microorganism of *Clostridium*]

Figure 1:
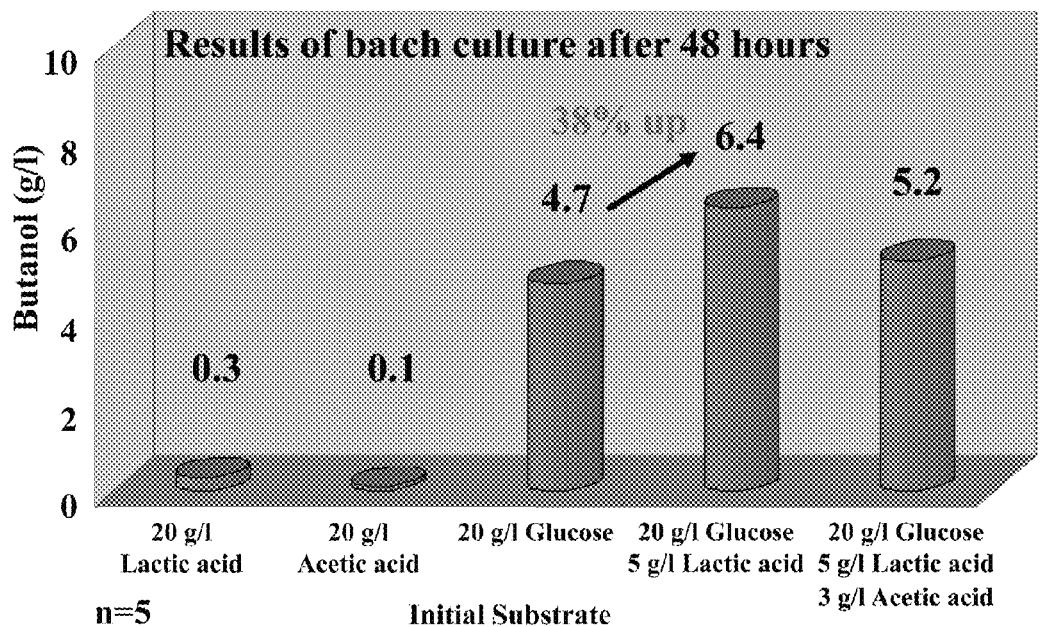
FIG. 1 is a graph showing the results of butanol production with growing cells in which lactic acid and/or acetic acid were/was added.

In the present invention, unless otherwise stated, the term "microorganism which belongs to the genus *Clostridium* and is capable of producing butanol" refers to a microorganism which is fermentable by ABE fermentation or butanol-isopropanol fermentation and belongs to the genus *Clostridium*. The "microorganism which belongs to the genus *Clostridium*" includes *Clostridium saccharoperbutylacetonicum, Clostridium beijerinckii, Clostridium acetobutylicum, Clostridium saccharoacetobutylicum, Clostridium aurantibutyricum, Clostridium pasteurianum, Clostridium sporogenes, Clostridium cadaveris*, and *Clostridium tetanomorphum*. The *Clostridium acetobutylicum* includes *Clostridium acetobutylicum* ATCC 824, which is a type strain.

In the present invention, a publicly-known microorganism which belongs to the genus *Clostridium* can be used. In the present invention, a publicly-known bacterial strain which belongs to *Clostridium saccharoperbutylacetonicum, Clostridium beijerinckii* or *Clostridium acetobutylicum* can suitably be used; examples include the following strains: *Clostridium saccharoperbutylacetonicum* N1-4 (ATCC 13564), which produces butanol at high production rate; *Clostridium beijerinckii* NCIMB8052, the genome of which has been completely sequenced, and *Clostridium acetobutylicum* IFO13498. These are commercially available.

The "microorganism which belongs to the genus *Clostridium* and is capable of producing butanol" of the present invention also includes a microorganism obtained by transformation by genetic manipulation or the like of a wild-type microorganism which belongs to the genus *Clostridium*, as long as the microorganism is capable of producing butanol and has a metabolic pathway in which lactic acid and/or acetic acid are/is produced as an intermediate product. For example, it is reported that the butanol production was increased when an expression vector was constructed by cloning a gene of molecular chaperone which repaired a denatured protein to recover the function thereof with a plasmid which was replicable by acetone-butanol-ethanol-producing bacteria, and the chaperone gene was overexpressed (Tomas C A, Welker N E, Papoutsakis E T., Appl Environ Microbiol. 69(6): 4951-4965 (2003)). These are also included in the "microorganism which belongs to the genus *Clostridium* and is capable of producing butanol" of the present invention.

The "microorganism which belongs to the genus *Clostridium* and is capable of producing butanol" of the present invention also includes: a transformant in which a gene encoding an enzyme having acetyl-CoA acetyltransferase activity, a gene encoding an enzyme having β-hydroxybutyl-CoA-dehydrogenase activity, a gene encoding an enzyme having 3-hydroxybutyryl-CoA-dehydratase activity, a gene encoding an enzyme having butyryl-CoA-dehydrogenase activity, a gene encoding an enzyme having butyrylaldehyde dehydrogenase activity, and a gene encoding an enzyme having butanoldehydrogenase activity, each of which is derived from a microorganism which belongs to the genus *Clostridium*, have been introduced into various host microorganisms (JP 2009-39031 A); and a recombinant microbial host cell comprising at least one DNA molecule encoding a polypeptide that catalyzes a substrate to product conversion selected from the group consisting of: a) acetyl-CoA to acetoacetyl-CoA b) acetoacetyl-CoA to 3-hydroxybutyryl-CoA c) 3-hydroxybutyryl-CoA to crotonyl-CoA d) crotonyl-CoA to butyryl-CoA e) butyryl-CoA to butyraldehyde and f) butyraldehyde to 1-butanol; wherein the at least one DNA molecule is heterologous to said microbial host cell and wherein said microbial host cell produces 1-butanol (WO 2007/041269 (JP 2009-509541 A)). The genetic manipulation may be performed using a publicly-known method. For example, methods for introducing and expressing a vector or foreign gene of various microorganisms are described in many experiment manuals (e.g., Sambrook, J. & Russel, D. W. Molecular Cloning: A Laboratory Manual (3rd Edition) CSHL Press, 2001, or Ausubel, F. et al. Current protocols in molecular biology. Green Publishing and Wiley Interscience, New York, 1987), and vector selection, gene introduction, and expression can be performed in accordance with these manuals.

In the present invention, unless otherwise stated, the term "butanol" refers to 1-butanol. In the present invention, butanol may be produced together with acetone and/or ethanol.

In ABE fermentation, typically, acetic acid and butyric acid are produced during a logarithmic phase of cell growth and the metabolic system is changed significantly during a resting phase (also referred to as "stationary phase"), during which cell growth is stopped, and acetone and butanol will be produced. In the present invention, butanol production can be performed efficiently using growing cells or resting cells of a microorganism of the genus *Clostridium*.

The state of a microorganism of the genus *Clostridium* may be set to a growing state or resting state by adding or not adding nutrients (nitrogen source and/or minerals) required for growth to a medium in which the microorganism is maintained. Specifically, when a resting state is desired, the microorganism may be placed in a medium free of required nutrients, typically nitrogen source. Further, there is a report that when the intracellular ppGpp level is maintained high by inducing guanosine tetraphosphate (ppGpp), which is an intracellular messenger, cell division is inhibited, and amino acid fermentation is promoted (Imaizumi A, Kojima H, Matsui K., J. Biotechnol. 125(3): 328-37, 2006). Such a method may also be used in the present invention.

Advantages of resting cells are that the cells can be reused; that a production system with excellent operational stability can be constructed; and that since butanol is produced in a manner that is not associated with cell growth during the resting phase, the production of by-products associated with cell growth is small.

In the present invention, unless otherwise stated, the term "medium (media)" refers to a culture medium or a reaction medium for artificially maintaining, growing or increasing a microorganism.

The medium for use in the butanol production of the present invention contains saccharides assimilable by a microorganism which belongs to the genus *Clostridium*, lactic acid and/or acetic acid as substrates.

As used herein, the term "as a substrate" or "as substrates" regarding a component contained in a medium for a microorganism of the genus *Clostridium* means that the component is contained in an amount (concentration) that can be used as a nutrient source by the microorganism, unless otherwise stated.

In the present invention, unless otherwise stated, the term "lactic acid" (IUPAC name is 2-hydroxypropanoic acid; it is also referred to as α-hydroxypropanoic acid) refers to lactic acid selected from the group consisting of D-lactic acid, L-lactic acid, and a mixture thereof. In the present invention, unless otherwise stated, the term "mixture" of D-lactic acid and L-lactic acid refers to lactic acid having less than 99% optical purity (also referred to as "enantiomeric excess"; this is a value obtained by subtracting the amount of a substance contained in smaller amount from the amount of a substance contained in greater amount and then dividing the difference by the total amount of substance). The mixture includes a racemic mixture in which D-lactic acid and L-lactic acid are contained in the same amount (optical purity: 0).

The "saccharides assimilable by a microorganism of the genus *Clostridium*" in the present invention include various edible or inedible saccharides composed of hexose or pentose units, such as glucose, fructose, galactose, xylose, arabinose, trehalose, mannitol, lactose, maltose, salicin, cellobiose, mannose, rhamnose, ribose, starch (soluble starch, sago starch, tapioca starch, corn starch, potato starch, wheat starch), dextrin, and xylan.

A person skilled in the art could appropriately determine assimilability of a microorganism of the genus *Clostridium* using a commonly-used method for the determination of assimilability. For example, a medium containing 1% by weight of saccharides as a carbon source is inoculated with a microorganism of the genus *Clostridium* and maintained for one to several days at a suitable temperature, and if a difference in absorbance at 660 nm from a control which is free of a carbon source is 0.3 or greater, it is determined as being "assimilable."

A typical example of saccharides assimilable by a microorganism of the genus *Clostridium* is glucose.

In the present invention, when a microorganism of the genus *Clostridium* is in a growing state, components contained as substrates in the culture medium are glucose and lactic acid. In some cases, it is preferable not to add acetic acid. When the microorganism of the genus *Clostridium* is in a resting state, components contained as substrates in the reaction medium are glucose and acetic acid, preferably glucose, lactic acid and acetic acid. In any case, lactic acid to be added is preferably a mixture of L-lactic acid and D-lactic acid.

The medium for a microorganism of the genus *Clostridium* may contain other various nutrients in addition to glucose, lactic acid and/or acetic acid. Culture media or reaction media for a microorganism of the genus *Clostridium* that can be used are: PG culture medium: About 1 L of distilled water is added to 200 g of chopped potato, and the mixture is boiled over gentle heat for 30 to 40 minutes and thereafter filtered through double gauze. Glucose is added to the filtrate at 20 g/l, and then distilled water is added to give the total amount of 1 L.
TYA culture medium: 4% glucose, 0.05% monopotassium phosphate, 0.03% magnesium sulfate heptahydrate, 0.001% iron sulfate heptahydrate, 0.3% ammonium acetate, 0.2% yeast extract, 0.6% tryptone
TY culture medium: 1% Bacto-tryptone, 1% Bacto-yeast extract, 0.5% sodium chloride, pH 7.0
Nitrogen-free medium (phosphate medium): 2% glucose, 0.05% monopotassium phosphate, 0.001% iron sulfate heptahydrate In the present invention, the concentration of glucose in an initial medium (medium at the beginning of the culture or reaction; none of the components has been consumed by the microorganism) is, for example, 2.5 g/l to 50 g/l, preferably 5 g/l to 40 g/l, more preferably 10 g/l to 30 g/l. The concentration of lactic acid in an initial culture medium is, for example, 0.5 g/l to 30 g/l, preferably 1 g/l to 15 g/l, more preferably 2.5 g/l to 7.5 g/l. The concentration of acetic acid in an initial culture medium is, for example, 0.3 g/l to 25 g/l, preferably 0.75 g/l to 12 g/l, more preferably 1.5 g/l to 6 g/l.

In the present invention, the molar ratio of glucose to lactic acid is, for example, 2:0.1 to 2:10, preferably 2:0.3 to 2:3, more preferably 2:0.5 to 2:2. In the case of using acetic acid, the molar ratio of lactic acid to acetic acid is, for example, 1:0.1 to 1:10, preferably 1:0.3 to 1:3, more preferably 1:0.5 to 1:2.

In a case of using saccharides assimilable by a microorganism of the genus *Clostridium* other than glucose, a person skilled in the art could determine an appropriate concentration of the saccharides in a medium and an appropriate ratio of saccharides to other components by reference to a preferred concentration and a preferred ratio to other components in the case of glucose.

According to studies conducted by the present inventors, a molar ratio of glucose to lactic acid of 2:1, or a molar ratio of lactic acid to acetic acid of 1:1 in the case of using acetic acid, was especially suitable for butanol production. The fact that the molar ratio of lactic acid to acetic acid of 1:1 is suitable indicates that a fermentation product of hetero-lactic acid fermentation can suitably be used directly as a raw material of biobutanol.

As to conditions for implementing the present invention other than the above substrates, a person skilled in the art could appropriately determine by applying conditions employed in conventional butanol production by a microorganism of the genus *Clostridium*. The culture/reaction temperature may be 30° C. to 37° C., which in general is an optimum temperature for a microorganism of the genus *Clostridium*. The culture/reaction time may be several hours to several days, for example 1 to 3 days. A method of feeding the culture medium/reaction medium is not particularly limited, and the culture medium/reaction medium may be fed by a batch process (nutrient components are added to the medium at the beginning and no replenishment will be conducted) or by a fed-batch process (batch process in which a culture medium/reaction medium containing a substrate is fed continuously or intermittently without withdrawing the culture medium/reaction medium) (Examples 1 and 2).

According to studies conducted by the present inventors, when lactic acid in which every carbon was substituted with $^{13}C$ stable isotope was used in butanol production using a microorganism of the genus *Clostridium*, it was confirmed that butanol having a molecular weight that was greater by 2 than usual, i.e., butanol with a molecular weight of 76 in which there are two $^{13}C$ contained, was produced (Example 3). On the basis of the metabolism of ABE fermentation, it is considered that $^{13}C_3$ lactic acid is converted into acetyl-CoA through pyruvic acid, forms acetoacetyl-CoA with acetyl-CoA derived from glucose ($^{12}C$), and finally is converted into butanol having two $^{13}Cs$ (formula below).

[Formula 1]

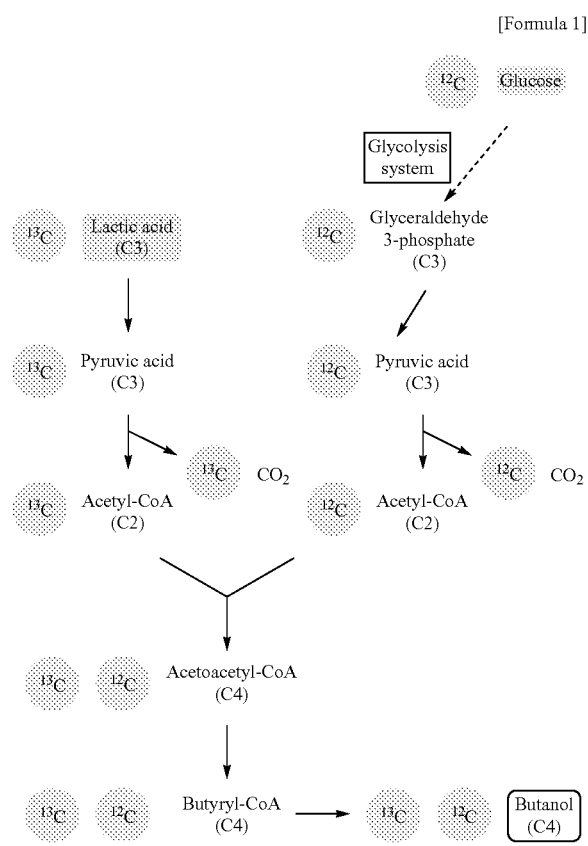

The present invention in which lactic acid and/or acetic acid are/is added as a substrate in butanol production is also applicable to a continuous fermentation process in which butanol is extracted continuously by a gas-stripping process (Bioprocess and Biosystems Engineering, 27, 207-214, 2005), a method of producing butanol by immobilizing bacteria of the genus *Clostridium* (Pakistan Journal of Biological Sciences, 9, 1923-1928, 2006, and Applied Biochemistry and Biotechnology, 113-116, 887-898, 2004), and a technique of a continuous fermentation process in which high-concentration cells of bacteria of the genus *Clostridium* are used and recycled (Journal of Biotechnol, 120, 197-206, 2005).

Advantages of addition of lactic acid and/or acetic acid in butanol production using a microorganism of the genus *Clostridium* compared with the case of adding butyric acid are that 1) prices are low, and that 2) lactic acid and acetic acid are easy to handle as raw materials of biobutanol because they are obtained at higher concentrations than that of butyric acid in production by fermentation. An advantage of addition of lactic acid compared with addition of butyric acid is that when a microorganism of the genus *Clostridium* metabolizes lactic acid, reduction power required for butanol synthesis is provided simultaneously.

[Combination with Lactic Acid Fermentation, Etc.]

Lactic acid and/or acetic acid in the present invention may be a lactic acid fermentation product using lactic acid bacteria and/or an acetic acid fermentation product using acetic acid bacteria.

In the present invention, unless otherwise stated, the term "lactic acid bacteria" refers to a group of bacteria which produce a large amount of lactic acid (50% or greater of acid produced through carbohydrate fermentation), propagate well in a culture medium containing carbohydrates, are gram-positive, have no motility, and form no spore. The lactic acid bacteria in the present invention include microorganisms which belong to the genus *Lactobacillus*, microorganisms which belong to the genus *Bifidobacterium*, microorganisms which belong to the genus *Enterococcus*, microorganisms which belong to the genus *Lactococcus*, microorganisms which belong to the genus *Pediococcus*, and microorganisms which belong to the genus *Leuconostoc*.

As to lactic acid bacteria, there are homo-lactic acid fermentation type which produce lactic acid using glucose in accordance with the homofermentative system and hetero-lactic acid fermentation type which produce lactic acid and acetic acid in accordance with the heterofermentative system. Either of them can be applied to the present invention. As to homofermentative type, it is preferable to apply lactic acid bacteria which ferment a mixture of D-lactic acid and L-lactic acid.

In an especially preferred embodiment of the present invention, the method includes a step of producing lactic acid and/or acetic acid using lactic acid bacteria capable of homo-lactic acid fermentation and also capable of producing L-lactic acid and D-lactic acid, or using lactic acid bacteria capable of hetero-lactic acid fermentation; and culturing a microorganism which belongs to the genus *Clostridium* in a culture medium containing glucose and the resulting lactic acid and/or acetic acid as substrates to produce butanol.

"Acetic acid bacteria" in the present invention include microorganisms which belong to the genus *Acetobacter* (e.g., *Acetobacter aceti, Acetobacter orientalis, Acetobacter pasteurianus, Acetobacter xylinum*), microorganisms which belong to the genus *Acidiphilium*, microorganisms which belong to the genus *Acidisphaera*, microorganisms which belong to the genus *Acidocella*, microorganisms which belong to the genus *Acidomonas*, microorganisms which belong to the genus *Asaia*, microorganisms which belong to the genus *Craurococcus*, microorganisms which belong to the genus *Gluconacetobacter*, microorganisms which belong to the genus *Gluconobacter*, microorganisms which belong to the genus *Kozakia*, microorganisms which belong to the genus *Muricoccus*, microorganisms which belong to the genus *Paracraurococcus*, microorganisms which belong to the genus *Rhodopila*, microorganisms which belong to the genus *Roseococcus*, microorganisms which belong to the genus *Rubritepida*, microorganisms which belong to the genus *Stella*, microorganisms which belong to the genus *Teichococcus*, and microorganisms which belong to the genus *Zavarzinia*.

Techniques for utilizing inedible biomass in lactic acid fermentation and acetic acid fermentation have been developed. By combining lactic acid fermentation or acetic acid fermentation with the method of producing butanol of the present invention, a practical system of producing butanol from inedible biomass can be constructed. The present inventors found a microorganism capable of producing lactic acid from cellooligosaccharides, a microorganism capable of producing lactic acid and acetic acid from xylan, xylooligosaccharides, xylose, which are major components of hemicellulose, and other microorganisms, and use of lactic acid fermentation products of these microorganisms in butanol production can be expected.

In the present invention, unless otherwise stated, the term "biomass (raw material)" refers to a recyclable, organismderived organic resources, excluding fossil resources. In the present invention, any biomass material that can be used as a raw material for lactic acid fermentation can be used without any limitation on the site of incidence, current state of use or form. Examples of biomass material include sugarcane, rice, corn, sweet potato, rapeseed, peanut, soybean, bagasse, leaf and stem, rice straw, rice chaff, wheat straw, mowed grass produced in large amount in golf courses and elsewhere, remaining wood on forest land, timber from forest thinning, oil palm timber, scrap wood from sawmill (e.g., timber offcut, sawdust, bark), construction waste (wood waste), waste paper, feces and urine of livestock, residues from slaughterhouse, residues from fishery processing, organic biomass sludge produced as waste, spent liquor, residues from food processing, used edible oil, raw garbage, sewage sludge, fish and shellfish, seaweed, and phytoplankton.

In the present invention, unless otherwise stated, the term "edible biomass" (also referred to as "food biomass") (raw material) refers to biomass material which can also be used as food for human or livestock. The edible biomass includes sugarcane, rice, corn, and sweet potato.

In the present invention, unless otherwise stated, the term "inedible biomass (raw material)" refers to biomass material other than edible biomass material. Application of inedible biomass material to the present invention is preferred.

Regarding lactic acid fermentation from inedible biomass material, a person skilled in the art can refer to the following papers of the present inventors:

(1) Lactic acid fermentation from xylose: K. Tanaka, A. Komiyama, K. Sonomoto, A. Ishizaki, S. J. Hall and P. F. Stanbury. Two different pathways for D-xylose metabolism and the effect of xylose concentration on the yield coefficient of L-lactate in mixed-acid fermentation by the lactic acid bacterium *Lactococcus lactis* IO-1, Appl. Microbiol. Biotechnol., 60 (1-2), 160-167 (2002 October);

(2) Lactic acid fermentation from xylooligosaccharides: Hitomi Ohara, Michiko Owaki & Kenji Sonomoto. Xylooligosaccharides fermentation with *Leuconostoc lactis*, J. Biosci. Bioeng., 101(5), 415-420 (2006 May 25);

(3) Lactic acid fermentation from xylose: Hitomi Ohara, Michiko Owaki & Kenji Sonomoto. Calculation of metabolites from xylose in *Lactococcus lactis*, J. Biosci. Bioeng., 103(1), 92-94 (2007.1.25); and (4) Lactic acid fermentation from xylose: Mugihito Oshiro, Hideaki Shinto, Yukihiro Tashiro, Noriko Miwa, Tatsuya Sekiguchi, Masahiro Okamoto, Ayaaki Ishizaki & Kenji Sonomoto. Kinetic modeling and sensitivity analysis of xylose metabolism in *Lactococcus lactis* IO-1, J. Biosci. Bioeng., 108(5), 376-384 (2009 Nov. 25).

The following papers can also be referred to:
(5) Production of lactic acid from cellulose by simultaneous saccharification and fermentation: S. Abe and M. Takagi. Simultaneous saccharification and fermentation of cellulose to lactic acid, Biotechnol. Bioeng., 37, 93-96 (1991);
(6) Production of lactic acid from cellulose by simultaneous saccharification and fermentation: K. V. Venkatesh. Simultaneous saccharification and fermentation of cellulose to lactic acid, Bioresour. Technol., 62, 91-98 (1997); and
(7) Lactic acid bacteria which directly assimilate xylan: M. Ishikawa, K. Nakajima, Y. Itamiya, S. Furukawa, Y. Yamamoto and K. Yamasato. *Halolactibacillus halophilus* gen. nov., sp. nov. and *Halolactibacillus miurensis* sp. nov., halophilic and alkaliphilic marine lactic acid bacteria constituting a phylogenetic lineage in Bacillus rRNA group 1, Int. J. Syst. Evol. Microbiol., 55, 2427-2439 (2005).

As to acetic acid fermentation from inedible biomass material, the following papers can be referred to:
(8) Cai S, Dong X.: *Cellulosilyticum ruminicola* gen. nov., sp. nov., isolated from yak rumen contents, and reclassification of *Clostridium lentocellum* as *Cellulosilyticum lentocellum* comb. nov. Int J Syst Evol Microbiol. 2009 in press. August 6. [Epub ahead of print]; and (9) Yang S J, Kataeva I, Hamilton-Brehm S D, Engle N L, Tschaplinski T J, Doeppke C, Davis M, Westpheling J, Adams M W.: Efficient degradation of lignocellulosic plant biomass, without pretreatment, by the thermophilic anaerobe "Anaerocellum thermophilum" DSM 6725. Appl Environ Microbiol. July; 75(14):4762-9 (2009).

[Others]
Butanol obtained by the present invention may be added to gasoline or diesel fuel and used. In the present invention, unless otherwise stated, the term "diesel fuel" refers to a light oil which is refined from crude oil and is used as a fuel for diesel engine. A diesel fuel is sometimes referred to simply as "light oil."

Butanol obtained by the present invention may be isomerized to give iso-butanol or tert-butanol, or may be used as a raw material of various chemically-synthesized substance such as isoprene, isobutene, and butene.

EXAMPLES

The composition of each culture medium/reaction medium used in the Examples is as follows.
Composition of PG culture medium: 150 g/l potato, 0.50 g/l ammonium sulfate, 10 g/l glucose, 3.0 g/l calcium carbonate
Composition of TYA culture medium: 2 g/l yeast extract, 6.0 g/l tryptone, 3.0 g/l ammonium acetate, 10 prig/1 iron sulfate heptahydrate, 0.50 g/l potassium dihydrogen-phosphate, 0.30 g/l magnesium sulfate heptahydrate
Composition of TY culture medium (see Non-patent Document 2): 2 g/l yeast extract, 6.0 g/l tryptone, 2.5 g/l ammonium sulfate, 10 mg/l iron sulfate heptahydrate, 0.50 g/l potassium dihydrogen-phosphate, 0.30 g/l magnesium sulfate heptahydrate Phosphate medium (see Non-patent Document 3): 0.50 g/l monopotassium phosphate, 10 mg/l iron sulfate heptahydrate Example 1

Culture with Growing Cells in which Lactic Acid was Added

Using *Clostridium saccharoperbutylacetonicum* N1-4 (ATCC 13564) as ABE-producing bacteria, culture was performed by the following method.

(1) A PG culture medium was refreshed for 24 hours. (In particular, the PG culture medium inoculated with 3 g of sand containing spores was boiled for 1 minute in a boiling-water bath to allow the spores to sprout, and this was cultured under anaerobic conditions at 30° C. for 24 hours; the same procedure was repeated in the following Examples.)

(2) A TYA culture medium was inoculated with the culture broth of (1) at an inoculums rate of 10%, and pre-culture was performed for 15 hours.

(3) A TYA culture medium was inoculated with the culture broth of (2) at an inoculums rate of 10%, and main culture was performed for 19 hours. Then, bacteria were harvested to thereby obtain high-density bacterial cells.

(4) To 5 ml of TY culture medium in a large test tube, 3 ml of substrate (20 g/l of glucose (final concentration); 20 g/l of glucose and 5 g/l of lactic acid (D-lactic acid and L-lactic acid; unless otherwise stated, the same procedure was repeated in the following Examples) (final concentration); or 20 g/l of glucose, 5 g/l of lactic acid and 3 g/l of acetic acid (final concentration)) was added. Then, the culture medium was inoculated with 2 ml of the high-density bacterial cells to give a final concentration of about 5 g/l to 10 g/l based on dry cell weight, and batch culture was performed in a test tube for 48 hours with a total amount of 10 ml. The culture was conducted at 30° C. under anaerobic conditions at an initial pH of 5.5, and no pH control was carried out (this procedure was repeated in Examples 2 to 6).

(5) Sampling was performed after 0 and 48 hours.

(6) The concentrations of glucose and lactic acid were analyzed by HPLC, and the concentrations of acetic acid and butanol were analyzed by GC.

The results are shown in FIG. 1.

In the fermentation process using growing cells, the addition of lactic acid promoted the butanol production. Specifically, in the case in which lactic acid or acetic acid is used alone as a substrate in the 48-hour batch fermentation, the fermentation was not developed and almost no butanol was produced. On the contrary, in the case of using the mixed substrate in which lactic acid was added to glucose or the mixed substrate in which lactic acid and acetic acid were added to glucose, the butanol concentration was increased, compared with the case of glucose alone. Especially in the case of using the mixed substrate of glucose and lactic acid, the butanol concentration was increased by 38%, compared with the case of glucose alone. Note that inhibition of growth by acetic acid is considered as one of the reasons why the butanol production decreased in the case of using the mixed substrate in which lactic acid and acetic acid were added to glucose, compared with the case in which the mixed solvent of glucose and lactic acid was used.

Example 2

Fed-Batch Culture

In an attempt to acquire butanol at higher concentration, batch culture and fed-batch culture were performed by the following process using the same bacterial cells as those in Example 1.
(1) A PG culture medium was refreshed for 24 hours.
(2) A TYA culture medium was inoculated with the culture broth of (1) at an inoculums rate of 10%, and pre-culture was performed for 15 hours.
(3) The TYA culture medium was inoculated with the culture broth of (2) at an inoculums rate of 10%, and main culture was performed for 19 hours. Then, bacteria were harvested to obtain high-density bacterial cells.
(4) To 50 ml of TY culture medium in a 300-ml Erlenmeyer flask, 30 ml of substrate solution (20 g/l of glucose and 5 g/l of lactic acid (final concentration)) was added. Then, the culture medium was inoculated with 20 ml of high-density bacterial cells to give a final concentration of about 6 g/l based on dry cell weight, and a culture test was started with a total amount of 100 ml. In the fed-batch culture, 10 ml of substrate solution (200 g/l of glucose+50 g/l of lactic acid) was added 12 hours after the beginning of the culture.
(5) Sampling was conducted after 0, 4, 8, 12, 16, 20, 24, and 48 hours in the batch culture, or after 0, 4, 8, 12, 16, 20, 24, 32, 40, and 48 hours in the fed-batch culture.
(6) The concentrations of glucose and lactic acid were analyzed by HPLC, and the concentration of butanol was analyzed by GC.

Figure 2:
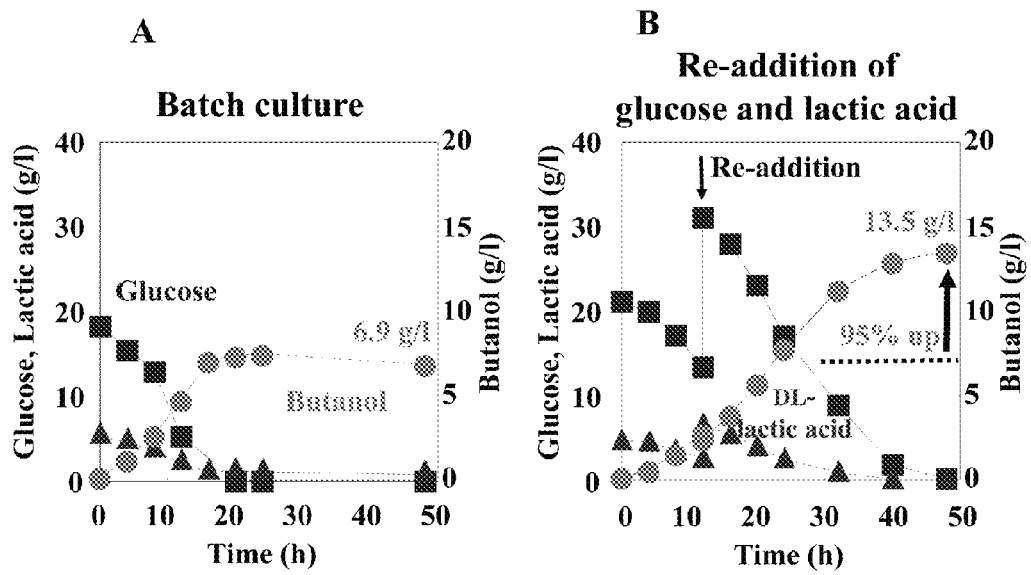
FIG. 2 is a graph showing the effect of re-addition of lactic acid in fed-batch culture (B) in comparison with batch culture (A).

The results are shown in FIG. 2. In the batch culture, the butanol concentration was 6.9 g/l after the 48-hour culture (FIG. 2A). On the other hand, in the fed-batch culture in which the substrate was added again after 12 hours, the glucose and lactic acid were consumed completely after 48 hours, and the butanol concentration was 13.5 g/l (FIG. 2B). In the fed-batch culture, the concentration was increased by 95%, compared with the case of batch culture.

From the above results it is considered that lactic acid and glucose were consumed to produce butanol.

It is a characteristic of butanol fermentation that the fermentation is stopped once the butanol concentration reaches ten and several grams per liter. Thus, even though the substrate was further added in the fed-batch culture, the butanol concentration did not increase significantly (data not shown).

Example 3

Confirmation by $^{13}C_3$ Lactic Acid

To determine whether butanol was produced from lactic acid in Example 2, batch culture was performed using lactic acid in which every carbon was substituted with $^{13}C$ stable isotope, and then whether butanol substituted with $^{13}C$ was produced was determined with a mass spectrograph. The process was as described below.
(1) A PG culture medium was refreshed for 24 hours.
(2) A TYA culture medium was inoculated with the culture broth of (1) at an inoculums rate of 10%, and pre-culture was performed for 15 hours.
(3) A TYA culture medium was inoculated with the culture broth of (2) at an inoculums rate of 10%, and main culture was performed for 19 hours. Then, bacteria were harvested to obtain high-density bacterial cells.
(4) To 1.5 ml of TY culture medium in a test tube, 0.9 ml of substrate (20 g/l of glucose and 5 g/l of $^{13}C$ L-lactic acid (final concentration)) was added. Then, the culture medium was inoculated with 0.6 ml of high-density bacterial cells to give a final concentration of about 10 g/l based on dry cell weight, and batch culture was performed in a test tube for 48 hours with a total amount of 3 ml. The culture was performed at 30° C. under anaerobic conditions at an initial pH of 5.5, and no pH control was carried out.
(5) Sampling was performed after 48 hours.
(6) Whether butanol substituted with $^{13}C$ was produced was determined with a mass spectrograph.

Figure 3:
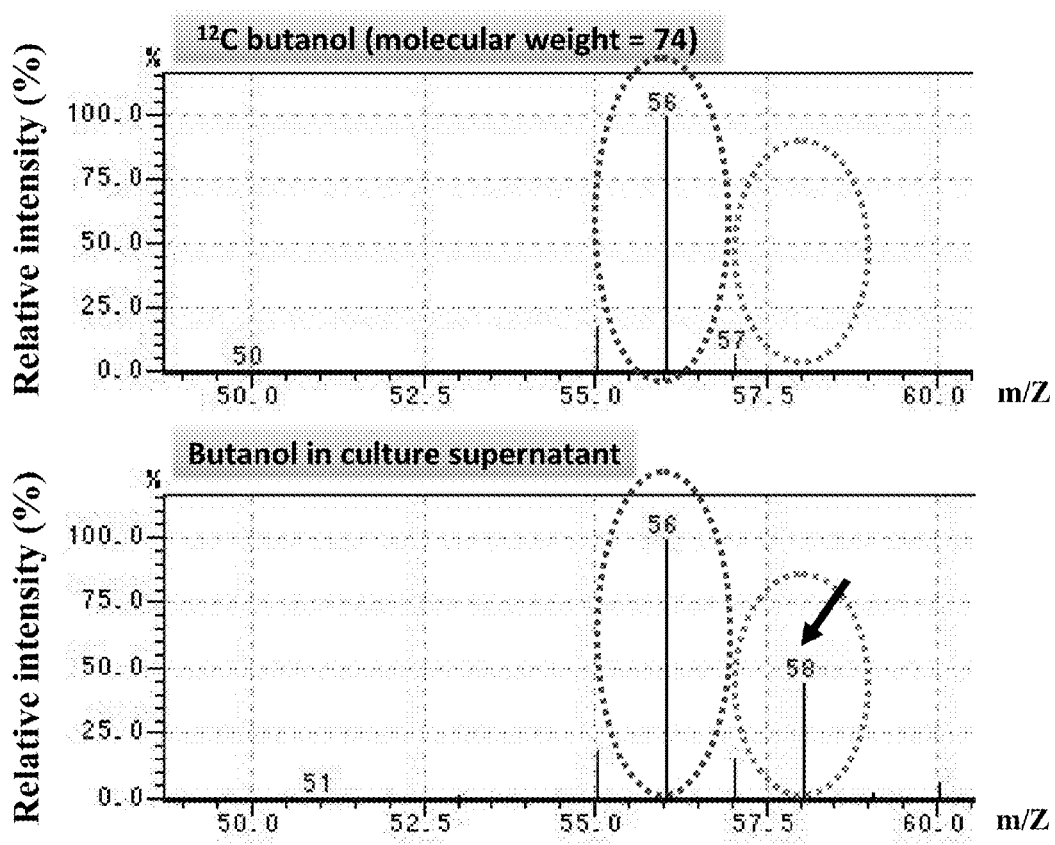
FIG. 3 shows the mass spectrum of butanol in a culture broth containing glucose and $^{13}C_3$ lactic acid as substrates. The arrow shows a peak of a fragment of butanol derived from $^{13}C_3$ lactic acid and $^{12}C$ glucose.

The mass spectra of $^{12}C$ butanol and butanol obtained by the culture in which $^{13}C_3$ lactic acid was added are shown in FIG. 3.

It is known that in general, dehydration reaction of water molecules tends to occur in primary alcohol, and a molecular ion peak does not tend to be observed in a mass spectrum. In the present analysis, no molecular ion peak of $^{12}C$ butanol (molecular weight: 74) was observed and, instead, a fragment peak of 56 (74−18) where dehydration occurred was observed. On the other hand, a peak of 58 (76−18) which was considered as being derived from $^{13}C_3$ lactic acid and glucose was observed in the mass spectrum of the butanol obtained by the culture, supporting that butanol was produced using lactic acid as a substrate.

From the results of the mass spectra, it is understood that 2 out of 4 butanol carbon atoms were derived from $^{13}C_3$ lactic acid. It is considered that through the metabolic pathway of ABE fermentation, acetoacetyl-CoA having two $^{13}Cs$ and 2 $^{12}Cs$ was synthesized from $^{13}C$ acetyl-CoA derived from $^{13}C_3$ lactic acid and $^{12}C$ acetyl-CoA derived from $^{12}C$ glucose and, as a result, butanol having a molecular weight that was increased by 2 was produced.

Example 4

Butanol Production Using Resting Cells

Butanol production was performed by the following process using resting cells.
(1) A PG culture medium was refreshed for 24 hours.
(2) A TYA culture medium was inoculated with the culture broth of (1) at an inoculums rate of 10%, and pre-culture was performed for 15 hours.
(3) A TYA culture medium was inoculated with the culture broth of (2) at an inoculums rate of 10%, and main culture was performed for 19 hours. Then, bacteria were harvested to obtain high-density bacterial cells.
(4) To 5 ml of phosphate medium in a large test tube, 3 ml of substrate (20 g/l of glucose (final concentration); 20 g/l of glucose and 5 g/l of lactic acid (final concentration); 20 g/l of glucose, 5 g/l of lactic acid and 3 g/l of acetic acid (final concentration); or 20 g/l of glucose and 3 g/l of acetic acid (final concentration)) was added, and thereafter 2 ml of high-density bacterial cells was added to give a final concentration of about 5 g/l to 10 g/l based on dry cell weight, and then batch reaction was performed in a test tube for 48 hours with a total amount of 10 ml.
(5) Sampling was performed after 0 and 48 hours.

(6) The concentrations of glucose and lactic acid were analyzed by HPLC, and the concentrations of acetic acid and butanol were analyzed by GC.

Figure 4:
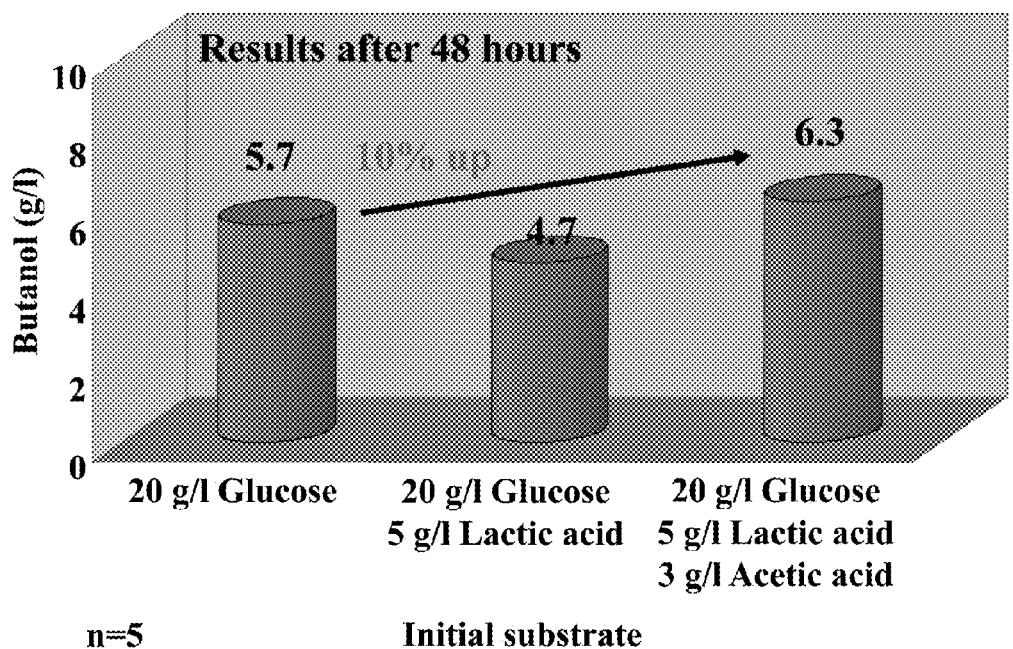
FIG. 4 is a graph showing the results of butanol production with resting cells in which lactic acid and/or acetic acid were/was added.

The results are shown in FIG. 4. In the case in which lactic acid was added, the butanol concentration was lower than that in the case of glucose alone. By further adding acetic acid, the butanol concentration was increased by 10% compared with the case of glucose alone. On the other hand, in the case of the system to which no lactic acid was added and only acetic acid was added, the butanol concentration 48 hours after the initiation of the reaction was 4.1 g/l, but the yield of butanol to the total substrate (C-mol/C-mol) was 0.54, and the yield of butanol to sugar (C-mol/C-mol) was 0.58; the yield was increased compared with the case of glucose alone. It was suggested that the effects of the addition of lactic acid and the addition of acetic acid were different from those in the fermentation process (the case of using growing cells).

It was considered that in the process using resting cells, acetic acid had the effect of promoting butanol production.

Example 5

Determination of Butanol Production Rate

Test Method
(1) A PG culture medium was refreshed for 24 hours.
(2) A TYA culture medium was inoculated with the culture broth of (1) at an inoculums rate of 10%, and pre-culture was performed for 15 hours.
(3) A TYA culture medium was inoculated with the culture broth of (2) at an inoculums rate of 10%, and main culture was performed for 19 hours. Then, bacteria were harvested to obtain high-density bacterial cells.
(4) To 50 ml of phosphate medium in a 300-ml Erlenmeyer flask, 30 ml of substrate solution (20 g/l of glucose (final concentration); or 20 g/l of glucose, 5 g/l of lactic acid and 3 g/l of acetic acid (final concentration)) was added. Then, 20 ml of high-density bacterial cells was added to give a final concentration of about 8 g/l based on dry cell weight, and then a reaction test was started with a total amount of 100 ml.
(5) Sampling was conducted after 0, 3, 6, 9, and 12 hours.
(6) The concentration of glucose was analyzed by HPLC, and the concentration of butanol was analyzed by GC.

Figure 5:
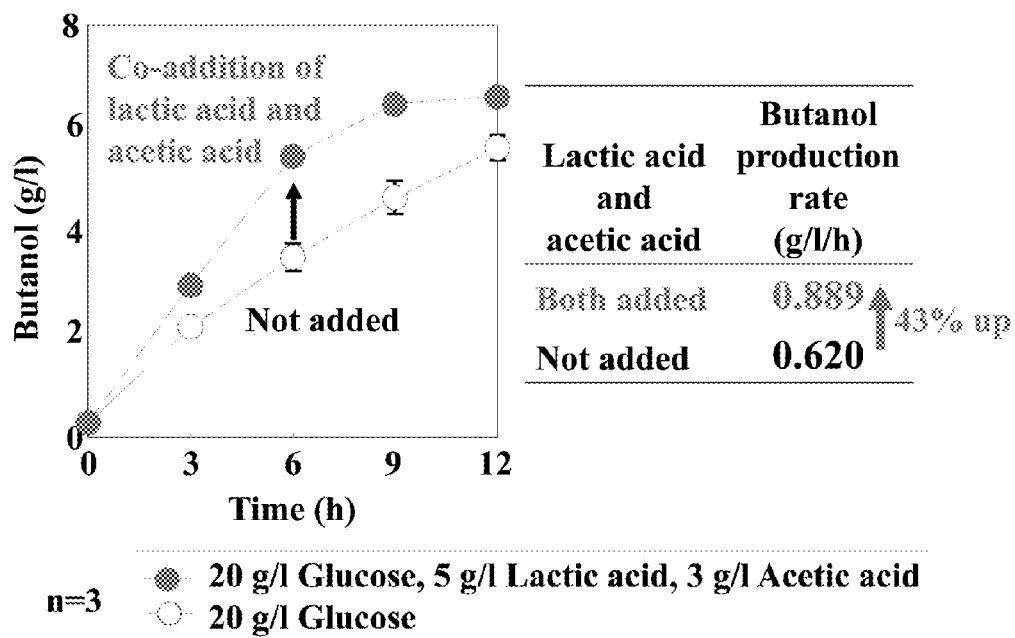
FIG. 5 is a graph showing that co-addition of lactic acid and acetic acid in the method in which the resting cells were used accelerated the butanol production rate.

The results are shown in FIG. 5. The butanol production rate ((the butanol concentration 3 h later (g/1)—butanol concentration (g/1) 0 h later)/3) up to 3 hours from the beginning of the reaction was 0.620 g/l/h in the case of using glucose alone as a substrate, but the butanol production rate was increased by co-addition of lactic acid and acetic acid to 0.889 g/l/h, which was an increase of 43%. Further, this value exceeded 0.808 g/l/h, which was the butanol production rate in the case of batch culture performed under optimized conditions using only glucose as a substrate, showing that co-addition of lactic acid and acetic acid was considerably effective for increasing the butanol production rate.

Example 6

Determination of Butanol Yield

The yield of butanol production by growing cells and the yield of butanol production by resting cells were compared by the following process.
(1) A PG culture medium was refreshed for 24 hours.
(2) A TYA culture medium was inoculated with the culture broth of (1) at an inoculums rate of 10%, and pre-culture was performed for 15 hours.
(3) A TYA culture medium was inoculated with the culture broth of (2) at an inoculums rate of 10%, and main culture was performed for 19 hours. Then, bacteria were harvested to obtain high-density bacterial cells.
(4) To 5 ml of acid culture medium (TY culture medium in the case of the growing cells, or phosphate medium in the case of the resting cells) in a large test tube, 3 ml of substrate (20 g/l of glucose (final concentration); 20 g/l of glucose and 5 g/l of lactic acid (final concentration); or 20 g/l of glucose, 5 g/l of lactic acid and 3 g/l of acetic acid (final concentration) was added. Then, 2 ml of high-density bacterial cells was inoculated (added) to give a final concentration of about 5 g/l to 10 g/l based on dry cell weight, and then batch culture (reaction) was performed in a test tube for 48 hours with a total volume of 10 ml.
(5) Sampling was performed after 0 and 48 hours.
(6) The concentrations of glucose and lactic acid were analyzed by HPLC, and the concentrations of acetic acid and butanol were analyzed by GC.

The results are shown in the table below.

TABLE 1

| Production method | Substrate | Butanol (g/l) | Yield of butanol to total substrate (C-mol/C-mol) | Yield of butanol to sugar (C-mol/C-mol) |
|---|---|---|---|---|
| Growing cells | Glc, Lac | 6.4 | 0.45 | 0.56 |
| Growing cells | Glc | 4.7 | 0.47 | 0.47 |
| Resting cells | Glc, Lac, Ace | 7.3 | 0.53 | 0.60 |
| Resting cells | Glc | 6.7 | 0.51 | 0.51 |

Despite addition of lactic acid or lactic acid and acetic acid, the yield of butanol to the total substrate was almost the same. However, the yield of butanol to glucose was increased by about 10%; from 0.47 to 0.56 in the case of the growing cells and from 0.51 to 0.60 in the case of the resting cells. This indicates that by adding lactic acid or acetic acid, the amount of butanol that can be produced from the same amount of glucose can be increased by about 10% in terms of C-mol. It was considered that the addition of lactic acid and/or acetic acid was effective for increasing the yield of butanol.

Example 7

Culture Using Other Microorganisms

Using acetone-butanol-ethanol (ABE) producing bacteria *Clostridium beijerinckii* NCIMB8052 (NCIMB Ltd.) and *Clostridium acetobutylicum* IFO13498 (The Institute for Fermentation, Japan), butanol production was performed using culture media containing glucose and lactic acid under the same culture conditions as those in Example 1. After 48-hour culture at 37° C. under anaerobic conditions, the amount of each product was measured using the culture supernatant.

The amount of butanol produced, the amount of glucose consumed, and the amount of lactic acid consumed which were measured 48 hours after the beginning of the culture are shown in the table below.

TABLE 2

|  |  | Acetone (g/l) | Butanol (g/l) | Ethanol (g/l) | ABE (g/l) | $Y_{butanol's}$ (C-mol/C-mol) | $Y_{abe's}$ (C-mol/C-mol) | Glucose consum. (g/l) | Lactate consum. (g/l) |
|---|---|---|---|---|---|---|---|---|---|
| C. beijerinckii | G20 | 1.98 | 3.43 | 0.63 | 6.05 | 0.36 | 0.62 | 15.25 | 0 |
| NCIMB8052 | G20, L5 | 0.73 | 4.82 | 0.38 | 5.93 | 0.33 | 0.40 | 20.88 | 2.56 |
| C. acetobutylicum | G20 | 0.02 | 0.75 | 0 | 0.76 | 0.40 | 0.41 | 3.00 | 0 |
| IFO13498 | G20, L5 | 0.25 | 2.24 | 0 | 2.49 | 0.25 | 0.28 | 11.08 | 3.34 |

Like the case of *Clostridium saccharoperbutylacetonicum* N1-4, consumption of glucose and lactic acid was also observed in the cases of *Clostridium beijerinckii* NCIMB8052 and *Clostridium acetobutylicum* IFO13498, and the amount of butanol produced was greater in the case in which lactic acid was added. From this result it became clear that butanol production using lactic acid as a substrate is possible with any ABE fermentation bacteria.

The invention claimed is:

1. A method of producing butanol, comprising
   producing lactic acid from inedible biomass material by a lactic acid bacterium; and
   producing butanol by a microorganism of the genus *Clostridium* in a medium containing, as substrates,
   a saccharide assimilable by the microorganism of the genus *Clostridium*, and
   0.5-30 g/L of the produced lactic acid,
   wherein a molecule of the produced butanol has at least one carbon atom derived from the produced lactic acid.

2. The method of claim 1, wherein the microorganism which belongs to the genus *Clostridium* is in a growing state, and the medium contains as substrates glucose and lactic acid.

3. The method of claim 1, wherein the microorganism which belongs to the genus *Clostridium* is in a resting state, and the medium contains as substrates glucose, lactic acid and acetic acid.

4. The method of claim 1, wherein the microorganism which belongs to the genus *Clostridium* is *Clostridium saccharoperbutylacetonicum*, *Clostridium beijerinckii*, and *Clostridium acetobutylicum*.

5. The method of claim 1, wherein the lactic acid is a mixture of L-lactic acid and D-lactic acid.

6. The method of claim 1, wherein the lactic acid is produced from inedible biomass material by a lactic acid bacterium which is capable of homo-lactic acid fermentation and is capable of producing L-lactic acid and D-lactic acid, or a lactic acid bacterium which is capable of hetero-lactic acid fermentation.

7. A method of producing a butanol-containing fuel, comprising the steps for the method of producing butanol as defined in claim 1, and adding the resulting butanol to a diesel fuel.

8. A method of producing a butanol-containing fuel, comprising the steps for the method of producing butanol as defined in claim 6, and adding the resulting butanol to a diesel fuel.

* * * * *